United States Patent [19]

Gansfried

[11] 4,114,043
[45] Sep. 12, 1978

[54] CABLE-SUPPORTING ARRANGEMENT FOR X-RAY TOMOGRAPHIC SCANNER

[75] Inventor: Myles Stephen Gansfried, Trumbull, Conn.

[73] Assignee: U.S. Philips Corporation, New York, N.Y.

[21] Appl. No.: 799,089

[22] Filed: May 20, 1977

[51] Int. Cl.² ............................................. A61B 6/02
[52] U.S. Cl. ................................ 250/445 T; 174/69; 191/12 C; 250/523
[58] Field of Search ............. 250/523, 445 T; 174/69; 191/12 C

[56] References Cited

U.S. PATENT DOCUMENTS

| | | | |
|---|---|---|---|
| 4,001,593 | 1/1977 | Wing et al. | 250/445 T |
| 4,063,104 | 12/1977 | Gadd | 250/523 |

Primary Examiner—Alfred E. Smith
Assistant Examiner—T. N. Grigsby
Attorney, Agent, or Firm—Frank R. Trifari; Rolf E. Schneider

[57] ABSTRACT

An axial tomographic scanner is provided with two separate chain-cable assemblies each carrying a fixed length of the cables leading to the scanner. One assembly includes a cable-incoming end anchored to the vertically arranged frame, the other end being anchored to the indexable rotatable plate. The other assembly also has one end anchored to this plate, the other, cable-outgoing end being anchored on the translatable yoke. Associated with and engaging each assembly is a translatable rotary member, which, when the plate is indexably rotated or the yoke is translated, is itself, respectively, translated and serves to take up the slack that would otherwise form in the respective assembly.

14 Claims, 8 Drawing Figures

CABLE-SUPPORTING ARRANGEMENT FOR X-RAY TOMOGRAPHIC SCANNER

BACKGROUND OF THE INVENTION

This invention relates to the support of flexible cables and the like leading to a piece of equipment including one or more movable parts so as to minimize undesirable flexing of such cables as well as to avoid undue interference with other components of such equipment. More particularly, the present invention provides a system for supporting a plurality of cables, tubes, and the like leading to X-ray equipment such as an axial tomographic scanner whereby undesirable bending, flexing, and other movement of the cables are essentially prevented.

The use of tomographic scanning to obtain cross-sectional or profile pictures of an object has become quite widespread. This type of X-ray equipment finds particular utility in providing detailed cross-sections of the internal tissue structure of various parts of the human body. As such, this procedure has developed into an extremely useful tool.

A typical axial tomographic scanner comprises essentially a source arranged to direct X-rays or other penetrating radiation through a planar slice of the object to be examined, means to detect such transmitted radiation after it has passed through the object, and mechanism to alternately translate and rotate the source and the detecting means about the object during such examination thereof. To enable such a device to be operated, suitable power cables, other electrical wiring, cooling-water tubes, and the like (all hereinafter generically designated as "cables") must be led on to the device. Because of the alternate or sequential translational and rotational motions to which such device is subjected during use, these cables necessarily undergo a varying degree of bending and flexing which may result not only in damage to the cables themselves but also in interruption of the operation of the device because of the resultant destruction of one part or another thereof. In addition, there is always the necessity, during operation of the device, of minimizing or preventing interference of the cables with the moving and other parts of the same.

Various arrangements have been suggested heretofore to control the degree of such bending and/or flexing of the cables and/or to prevent in so far as possible any interference of the cables with other components of the scanner. In practice, however, these arrangements have not proved entirely satisfactory and leave something to be desired.

BRIEF SUMMARY OF THE INVENTION

It has now been found that these disadvantages of such previously proposed systems can be effectively eliminated by means of the present invention, which provides an arrangement whereby, during operation of a tomographic scanner, the cables are bent or flexed so that the tension and the compression to which they are thereby subjected are substantially equalized and any slack that would otherwise result in such cables during any translational or rotational movement of the scanner is essentially prevented. In this manner the useful life of the cables is markedly increased, and no "loose" cable is present at any time to interfere with the operation of the scanner.

This objective is basically accomplished by providing two separate chain-cable assemblies each carrying a fixed length of the cables leading to the source of the X-rays or other penetrating radiation. One of such assemblies includes a cable-incoming end, which is anchored in place to the vertically arranged frame, the other end being anchored in place to the indexably rotatable plate of the scanner. The other of such assemblies also has one end anchored in place to this plate, the other, cable-outgoing end being anchored in place on the translatable yoke. Associated with and engaging the first assembly is a pair of vertically arranged rotary members, one of which is journalled on the frame and the other of which is journalled in a carriage movable horizontally with respect to such frame whereby, when the plate is indexably rotated, such other rotary member and its carriage are moved so as to take up the slack that would otherwise result in the first assembly. Similarly, associated with and engaging the second assembly is a horizontally arranged rotary member journalled in a carriage movable in parallel with respect to the yoke whereby, when the yoke is translated, such latter rotary member and its carriage are moved so as to take up the slack that would otherwise result in such second assembly.

Advantageously, each chain-cable assembly comprises a pair of parallel roller chains joined by a plurality of linearly spaced tie bars which support and are attached to the cables. At the same time each rotary member comprises a pair of sprockets transversely spaced so as to engage the parallel roller chains of its respective assembly.

Desirably, each anchoring arrangement includes a fixed bracket provided with a pair of apertures with a pin or spindle extending through each aperture. The inner end of each pin is attached to the corresponding end of its respective chain, the outer end being formed with a head or the like; and a suitable spring is associated with each pin between its head and the bracket. In this manner allowance is made for play in each chain-cable assembly.

The resulting scanner represents a tight operating device exhibiting little or no cable wear other than that from ordinary and regular usage.

BRIEF DESCRIPTION OF THE DRAWINGS

The invention will now be described in detail in connection with the accompanying drawings, in which.

DESCRIPTION OF THE PREFERRED EMBODIMENT

Figure 1:
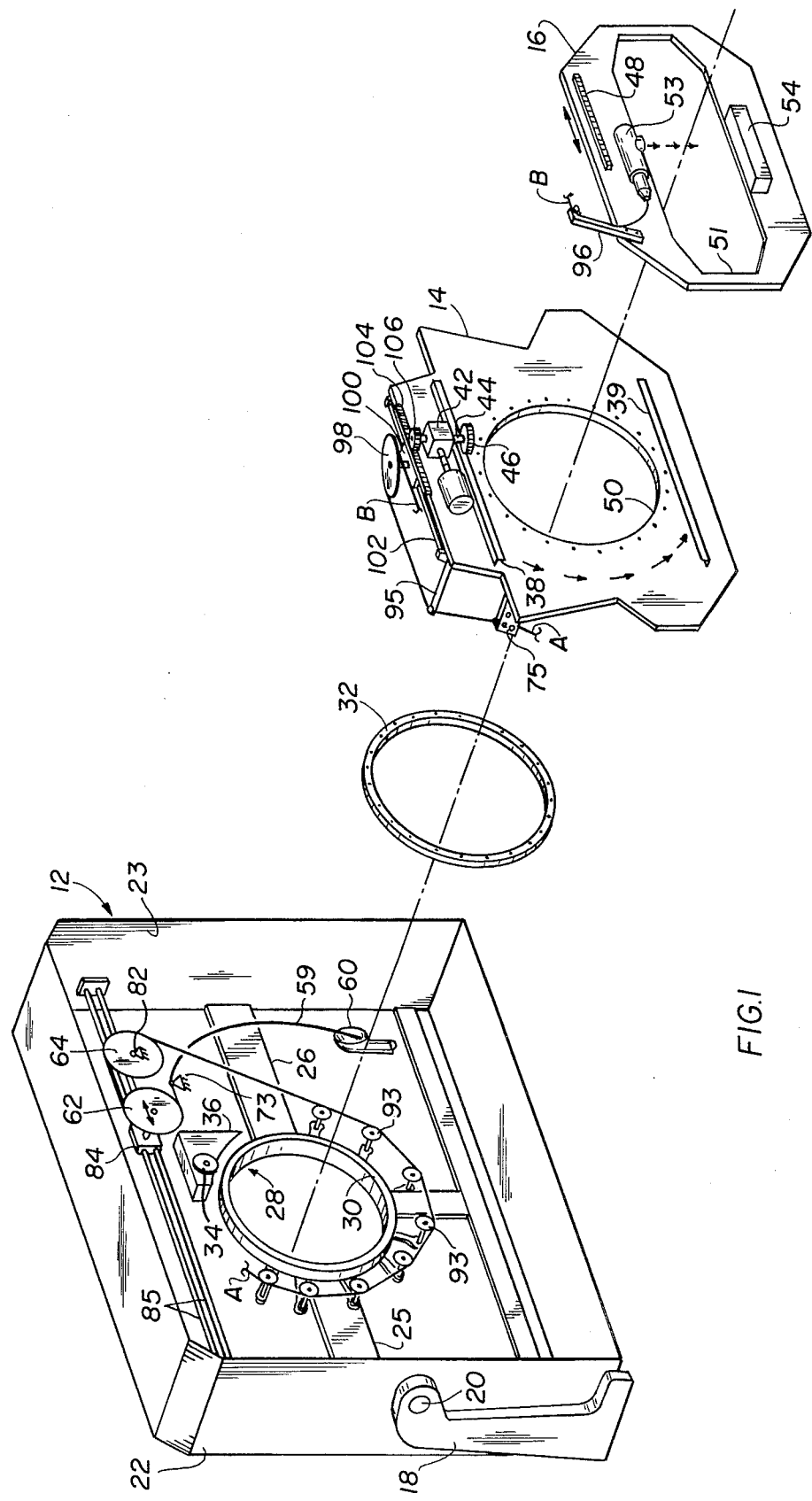
FIG. 1 represents an exploded schematic perspective view of a tomographic scanner embodying the present invention.

As shown in FIG. 1, the axial tomographic scanner basically comprises the vertically arranged frame 12, the indexably rotatable plate 14, and the back-and-forth translatable yoke 16. Frame 12 may be stationary or otherwise fixed in position by itself; or it may be mounted on a pair of oppositely disposed uprights 18 (only one of which is shown) by means of oppositely outwardly extending pivot rods 20 (again only one of which is shown). This latter arrangement enables the frame 12 to be slightly pivoted to the front or to the back as may be desired. In such case, of course, means (not shown) is provided to lock the frame in the position that is selected.

Extending from the vertical side walls 22 and 23 of frame 12 are two horizontally disposed cross-pieces 25 and 26, which centrally support the ring 28 provided with the frontwardly protruding flange 30. Rotatably surrounding this flange is the bull gear ring 32, which is attached to the plate 14. Pinion 34 is provided to drive gear ring 32 and is journalled in grear box 36 suitably affixed to cross-piece 26.

The front side of plate 14 is provided with the parallel rails 38 and 39, which slidingly engage corresponding rails (not shown) on the back side of yoke 16. Translational movement of yoke 16 is effected by means of motor 41, which is mounted on gear box 42. Extending vertically from such gear box is the shaft 44, on the lower end of which is mounted pinion 46 for engagement with rack 48 on the front side of yoke 16.

As indicated, plate 14 is provided with a central opening 50, and yoke 16 with a central opening 51. Thus, when the several basic pieces are assembled, the scanner is adapted to receive an object such as a human body that is to be scanned. Scanning is effected by means of X-rays or other penetrating radiation emanating from source 53 and detected by detector 54, with, of course, sequential translation of yoke 16 and indexed rotation of plate 14 by means of pinion 34. Motor 56 is mounted on gear box 36 for effecting such indexing action of pinion 34. To insure that the translational movement of yoke 16 and the indexed rotation of plate 14 occur in the desired sequence, a suitable electronic or other timing control 58 is connected to motors 41 and 56.

In order to operate the scanner, the appropriate cables 59 are led into the device at 60 upwardly onto a chain or belt 61 and then over the vertically arranged rotary members 63 and 64. Chain or belt 61 may be of any suitable type such as a timing belt but preferably comprises a pair of transversely spaced parallel roller chains 66 and 67 joined by a plurality of linearly separated tie bars 69. Similarly, each rotary member 63 and 64 may be of any suitable type such as a pulley (as when chain 61 comprises a timing belt) but preferably comprises a pair of sprockets 70 and 71 transversely spaced so as to engage the spaced roller chains.

A feature of the present construction is that, where the cables are in contact with the chain, the cables are fastened to the chains (as will be described further below) so as to form a chain-cable assembly of fixed length. Two such chain-cable assemblies are provided, one for use in connection with the rotatable indexing of the plate 14 and one for the translational movement of the yoke 16. The purpose in each instant instance is to prevent any slack that would otherwise be formed in the cables due to such indexing or translational movement, as will become apparent. To accomplish this objective, each end of each chain-cable assembly is fixed in position.

Figure 5:
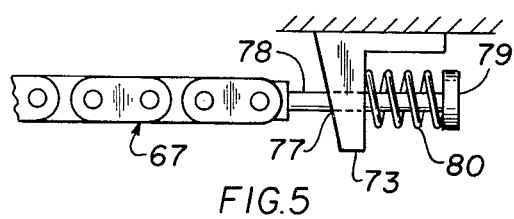
FIG. 5 is an enlarged detailed view of one of the chain-cable assembly anchoring means.
Figure 6A:
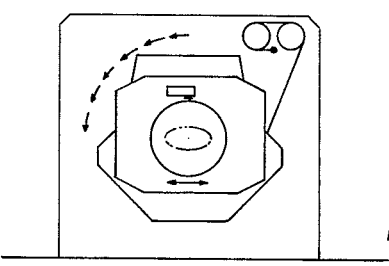
FIGS. 6A, 6B, and 6C are schematic views on a small scale to show the relative positions of the first chain-cable assembly when the scanner is in its initial position, has been rotated 90°, and has been rotated 180°, respectively.
Figure 6B:
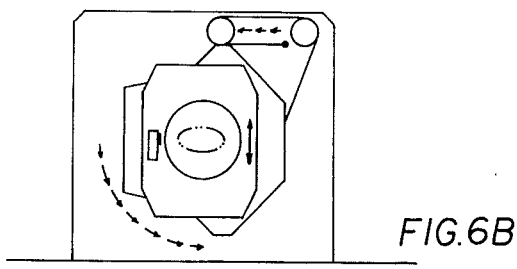
Figure 6C:
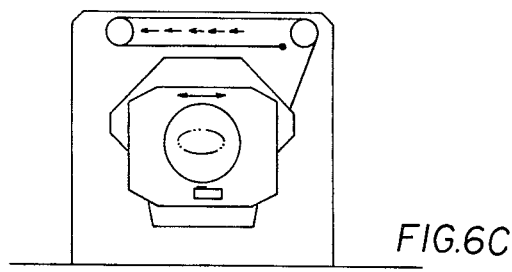

The chain-cable assembly utilized with the plate-indexing operation is anchored at its cable-incoming end to the bracket 73, which is affixed to the frame. The other end of such assembly is anchored to the bracket 75, which is affixed to the plate. Such anchoring may be accomplished in any suitable manner as, for example, the arrangement shown in FIG. 5. In such case the bracket such as bracket 73 is provided with a pair of apertures 77, through each of which a pin or spindle 78 extends. The inner end of each pin is attached to its corresponding roller chain 67 or 66; and its outer end is provided with a head 79, between which and the bracket a spring member 80 is positioned. Such spring member serves to absorb any shock resulting from variations in the sprockets and/or the roller chains.

Rotary member 64 is rotatably mounted on the frame as at 82. On the other hand, rotary member 63 is rotatably mounted on a carriage 84 which is slideably mounted on a pair of horizontal rods 85 supported by the frame. Motor 56, through the medium of gear box 36 and the attached gear box 87, drives timing belt 89 by means of a belt or chain 90. Carriage 84 being attached to timing belt 89 by clamp 91, rotary member 63 is thereby moved along rods 85 in one direction or the other.

Ring 28 is also provided with a plurality of linearly spaced, horizontally positioned fixed rotatably mounted rollers or idlers 93, which may take any appropriate form but which preferably each comprise a pair of idler sprockets spaced so as to engage the spaced roller chains 66 and 67. Advantageously, these idler sprockets are arranged in a circular pattern adjacent the periphery of the frame to facilitate the indexed rotation of the plate.

Figure 2:
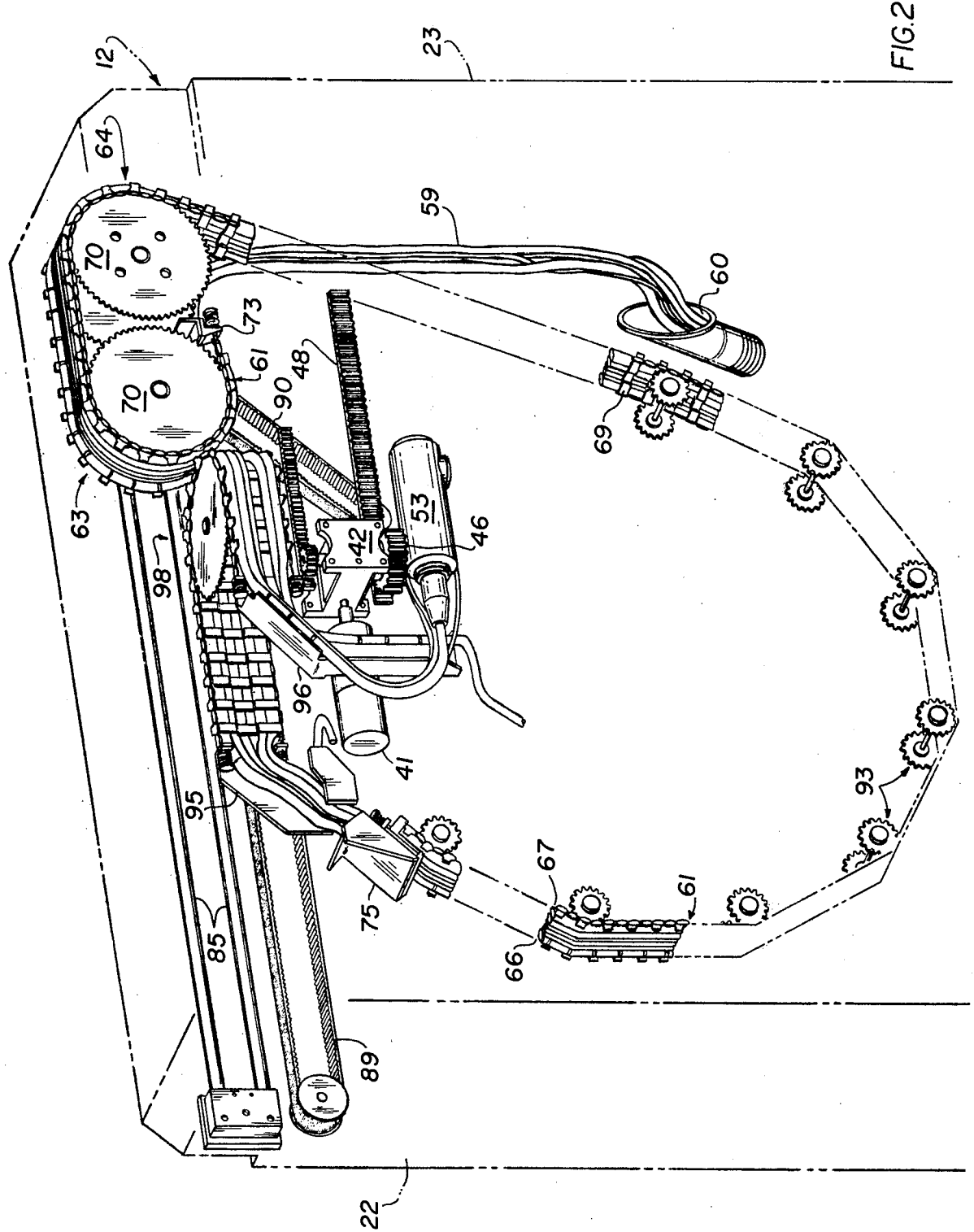
FIG. 2 is an enlarged schematic perspective front view of such scanner, with various parts omitted and with various other parts shown in broken lines.
Figure 3:
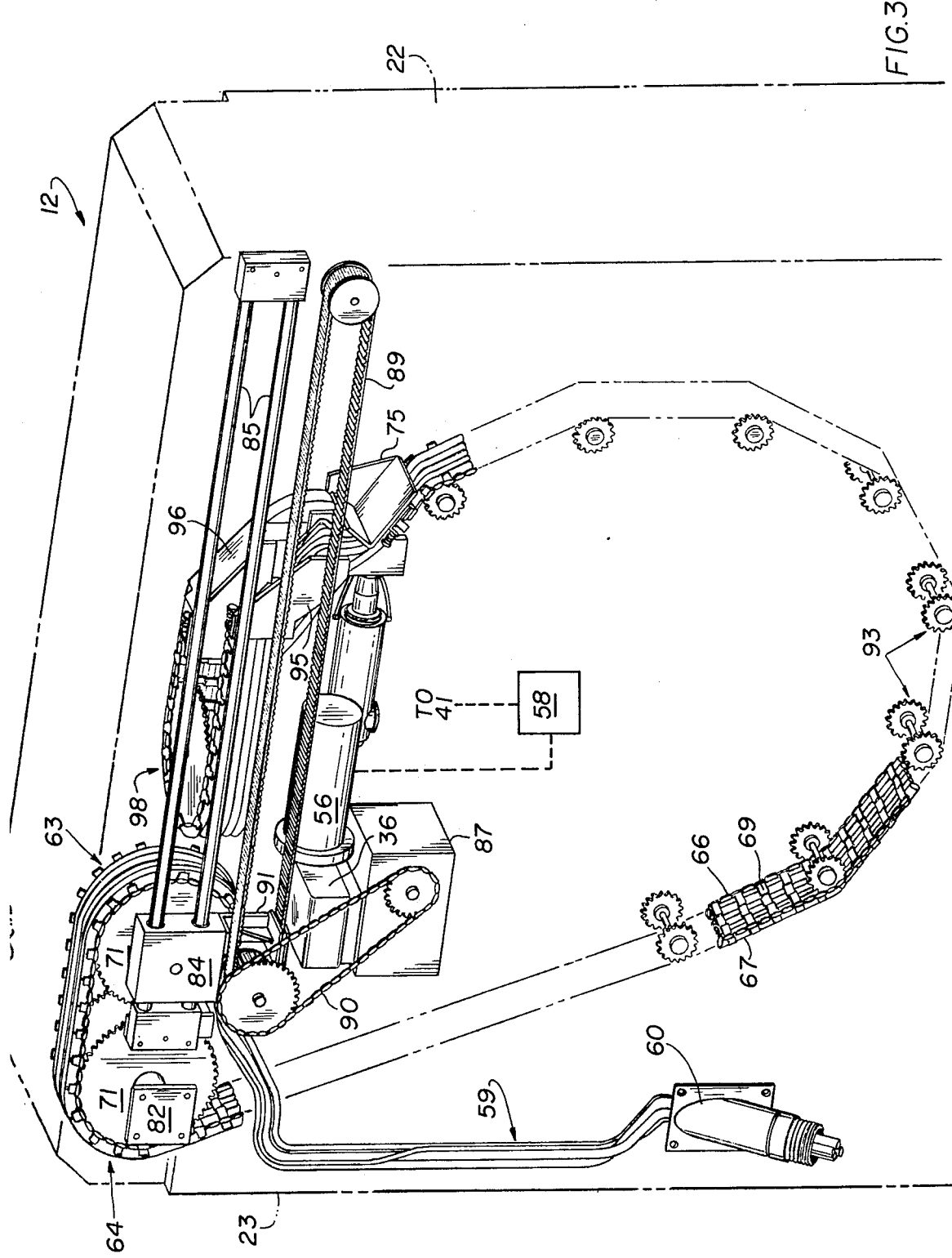
FIG. 3 is an enlarged schematic perspective rear view of the scanner, again with various parts omitted and with various other parts shown in broken lines.

In operation, then, each time the plate is indexed, rotary member 63 is also moved in the appropriate direction. With both rotary members 63 and 64 in the position shown in FIG. 2, indexed rotation of the plate 14 occurs in a counter-clockwise direction, as indicated in FIG. 1. Because of the simultaneous movement of rotary member 63 to the left (as viewed in FIG. 2), whatever slack that might result from such indexing is completely taken up by the loop formed by the leftward movement of rotary member 63. To be certain that this result is obtained, the timing belt to which carriage 84 is clamped is driven at a velocity corresponding to the linear equivalent of the velocity at which the instant chain-cable assembly is engaged by the rollers or idler sprockets.

The other chain-cable assembly, which is utilized with the yoke-translation operation, is anchored at one end to bracket 95, which is affixed to the frame. The other, cable - outgoing end of such assembly is anchored to the bracket 96, which is affixed to the yoke. This chain-cable assembly engages rotary member 98, which is rotatably mounted on carriage 100 slideably mounted on a pair of rods 102 supported by the plate. Carriage 100 is moved in one direction or the other by engagement of the rack 104 by pinion 106, which is mounted on the upper end of shaft 44. The relationship between rack-pinion 104-106 and rack-pinion 46-48 is such that carriage 100 is driven at a velocity equal to half that of the yoke. Thus, when plate 14 is driven to the right as viewed in FIG. 1, whatever slack that might result from such translation of the plate is completely taken up by the corresponding movement of rotary member 98.

In this manner, then, the cables are prevented from interfering with any other component or part of the scanner. In addition, the tie bars that extend between the spaced roller chains are so configured that the diameters of the various cables supported thereby are all on the pitch line of the spaced sprockets. With such arrangement the tension exerted on the outer half of each cable as it is flexed is equal to the compression exerted on the inner half of such cable so that cable wear is substantially reduced and a much longer cable life is obtained.

Figure 4:
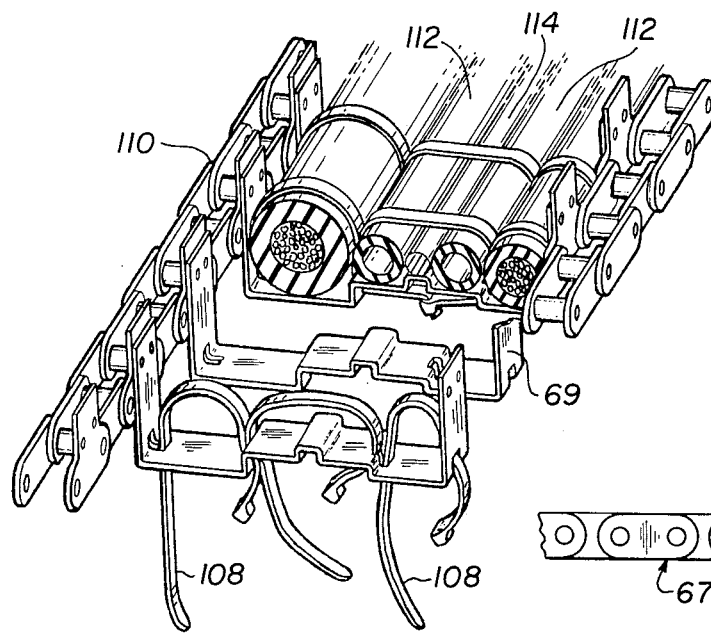
FIG. 4 is an enlarged perspective view of a chain-cable assembly, with the cables shown in section.

In order to provide each chain-cable assembly, each tie bar 69 is equipped with one or more tie straps 108 as shown in FIG. 4. Each such tie strap may hold only one cable such as the X-ray tube cable 110 in place; or it may hold more than one such cable in place, as with the water hose cables 112 and the intermediate ground cable 114. It will be appreciated, of course, that the configuration of the tie bars 69 will be governed basically by the number and/or the size of the cables supported thereby.

I claim:

1. Apparatus provided with a plurality of flexible cables mounted on a movable part, which comprises a fixed vertically arranged frame; a plate mounted on said frame for rotation about a horizontal axis, means for indexably rotating said plate; a movable member mounted on said plate for back-and-forth translational movement relative to said plate, means to effect back-and-forth translational movement of said movable member; a first chain-cable assembly carrying a fixed length of the cables, first means anchoring the cable-incoming end of said first assembly to said frame, second means anchoring the other end of said first assembly to said plate; a second chain-cable assembly carrying a separate fixed length of the cables, third means anchoring one end of said second assembly to said plate, fourth means anchoring the other, cable-outgoing end of said second assembly to said movable member; a pair of vertically arranged rotary members carried by said frame for engaging said first assembly, one of said rotary members being rotatably mounted on said frame and the other of said rotary members being rotatably mounted on a carriage movable horizontally with respect to said frame, said plate-rotating means being adapted to rotate said other rotary member and move its carriage so as to take up the slack that would otherwise be formed in said first assembly upon indexing of said plate; a plurality of linearly spaced small rollers rotatably mounted on said frame for engagement by said first assembly; a horizontally arranged rotary member carried by said plate for engaging said second assembly, said latter rotary member being rotatably mounted on a carriage movable parallelly with respect to said movable member, said moveable member-translating means being adapted to rotate said latter rotary member and move its carriage so as to take up the slack that would otherwise be formed in said second assembly upon translation of said movable member; and means to effect indexing of said plate and back-and-forth translational movement of said movable member in the desired sequence.

2. An axial tomographic scanner, which comprises a fixed vertically arranged frame; a plate mounted on said frame for rotation about a horizontal axis, means for indexably rotating said plate; a yoke mounted on said plate for back-and-forth translational movement relative to said plate, means to effect back-and-forth translational movement of said yoke; a source mounted on said yoke for directing penetrating radiation through an object to be scanned, a plurality of flexible cables leading to said source; a first chain-cable assembly carrying a fixed length of said cables, first means anchoring the cable-incoming end of said first assembly to said frame, second means anchoring the other end of said first assembly to said plate; a second chain-cable assembly carrying a separate fixed length of said cables, third means anchoring one end of said second assembly to said plate, fourth means anchoring the other, cable-outgoing end of said second assembly to said yoke; a pair of vertically arranged rotary members carried by said frame for engaging said first assembly, one of said rotary members being rotatably mounted on said frame and the other of said rotary members being rotatably mounted on a first carriage movable horizontally with respect to said frame, said plate-rotating means being adapted to rotate said other rotary member and move its carriage so as to take up the slack that would otherwise be formed in said first assembly upon indexing of said plate; a plurality of linearly spaced small rollers rotatably mounted on said frame for engagement by said first assembly; a horizontally arranged rotary member carried by said plate for engaging said second assembly, said latter rotary member being rotatably mounted on a second carriage movably parallelly with respect to said yoke, said yoke-translating means being adapted to rotate said latter rotary member and move its carriage so as to take up the slack that would otherwise be formed in said second assembly upon translation of said yoke; and means to effect indexing of said plate and back-and-forth translational movement of said yoke in the desired sequence.

3. A scanner according to claim 2, in which each chain-cable assembly comprises a pair of transversely spaced parallel roller chains joined by a plurality of linearly separated tie bars, the cables being supported by and attached to said tie bars; each rotary member comprises a pair of sprockets transversely spaced so as to engage the spaced roller chains of its respective assembly; and each small roller comprises a pair of roller sprockets spaced so as to engage the spaced roller chains of the first assembly.

4. A scanner according to claim 3, in which the plurality of linearly spaced idler sprocket pairs are arranged in a circular pattern on the frame.

5. A scanner according to claim 3, in which the cables are attached to each tie bar by a plurality of tie straps, each tie strap holding at least one cable in place on such tie bar.

6. A scanner according to claim 3, in which each tie bar has a configuration supporting the plurality of cables so that the diameter of each such cable is on the pitch line of the spaced sprockets.

7. A scanner according to claim 3, in which each anchoring means comprises a bracket fixed in place, said bracket being provided with a pair of apertures, a pin extending through each aperture, the inner end of each pin being attached to the corresponding end of its respective chain and the outer end of each pin being provided with a head, and spring means associated with each pin between its head and the bracket.

8. A scanner according to claim 2, in which the first carriage is slideably mounted on a pair of horizontal rods supported by the frame.

9. A scanner according to claim 8, in which said first carriage is affixed to a timing belt driven by the plate-rotating means at a velocity corresponding to the linear equivalent of the velocity at which the first assembly is engaged by said spaced small rollers.

10. A scanner according to claim 2, in which the second carriage is slideably mounted on a pair of rods supported by the plate.

11. A scanner according to claim 10, in which the yoke-translating means comprises a first rack mounted on the yoke, a first pinion engaging said first rack and driven by a motor, a second rack mounted on said second carriage, and a second pinion engaging said second rack and driven by said motor, the relationship between said two rack-and-pinion combinations being such that said second carriage is driven at a velocity equal to half that of the yoke.

12. A scanner according to claim 2, in which first rails are mounted on the yoke-facing side of said plate, and corresponding rails are mounted on the plate-facing side of said yoke for sliding engagement with said first rails.

13. A scanner according to claim 2, which includes means for detecting the penetrating radiation after it has passed through the object to be scanned.

14. A scanner according to claim 2, in which the penetrating radiation emitted by said source comprises X-rays.

* * * * *